US006316031B1

(12) United States Patent
Oshlack et al.

(10) Patent No.: US 6,316,031 B1
(45) Date of Patent: *Nov. 13, 2001

(54) STABILIZED CONTROLLED RELEASE SUBSTRATE HAVING A COATING DERIVED FROM AN AQUEOUS DISPERSION OF HYDROPHOBIC POLYMER

(75) Inventors: Benjamin Oshlack, New York; Frank Pedi, Jr., Yorktown Heights, both of NY (US); Mark Chasin, Manalapan, NJ (US)

(73) Assignee: Purdue Pharma LP, Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/469,478

(22) Filed: Dec. 22, 1999

Related U.S. Application Data

(60) Continuation of application No. 08/899,924, filed on Jul. 24, 1997, now Pat. No. 6,129,933, which is a division of application No. 08/667,052, filed on Jun. 20, 1996, now Pat. No. 5,681,585, which is a continuation-in-part of application No. 08/561,829, filed on Nov. 27, 1995, now Pat. No. 5,958,459, which is a continuation of application No. 08/086,248, filed on Jul. 1, 1993, now abandoned, which is a continuation-in-part of application No. 07/814,111, filed on Dec. 24, 1991, now Pat. No. 5,273,760.

(51) Int. Cl.$^7$ ..................................................... A61K 9/62
(52) U.S. Cl. ........................ 424/495; 424/461; 424/480; 424/494; 427/213.31
(58) Field of Search ................... 424/495, 461, 424/471, 480, 490, 494; 427/2.21, 213.31

(56) References Cited

U.S. PATENT DOCUMENTS

| | | | |
|---|---|---|---|
| 4,415,547 * | 11/1983 | Yu et al. ............................. | 424/469 |
| 4,587,118 * | 5/1986 | Hsiao ................................. | 424/459 |
| 4,634,587 * | 1/1987 | Hsiao ................................. | 424/495 |
| 4,786,509 * | 11/1988 | Chang et al. ........................ | 424/490 |
| 4,844,909 * | 7/1989 | Goldie et al. ....................... | 424/480 |
| 4,861,598 * | 8/1989 | Oshlack .............................. | 424/468 |
| 5,133,974 * | 7/1992 | Paradissis et al. .................. | 424/480 |
| 5,266,331 * | 11/1993 | Oshlack et al. ..................... | 424/468 |
| 5,273,760 * | 12/1993 | Oshlack et al. ..................... | 424/480 |
| 5,286,493 * | 2/1994 | Oshlack et al. ..................... | 424/468 |
| 5,472,712 * | 12/1995 | Oshlack et al. ..................... | 424/480 |
| 5,656,295 * | 8/1997 | Oshlack et al. ..................... | 424/468 |
| 5,670,172 * | 9/1997 | Buxton et al. ...................... | 424/495 |
| 5,672,360 * | 9/1997 | Sackler et al. ...................... | 424/490 |
| 5,681,585 * | 10/1997 | Oshlack et al. ..................... | 424/494 |
| 5,800,836 * | 9/1998 | Morella et al. ..................... | 424/489 |
| 5,958,459 * | 9/1999 | Chasin et al. ...................... | 424/490 |
| 5,968,551 * | 10/1999 | Oshlack et al. ..................... | 424/456 |
| 6,129,933 * | 10/2000 | Oshlack et al. ..................... | 424/495 |
| 6,143,322 * | 11/2000 | Sackler et al. ...................... | 424/459 |
| 6,165,503 * | 12/2000 | G.ang.ser.o slashed.d et al. | 424/463 |

* cited by examiner

*Primary Examiner*—Robert H. Harrison
(74) *Attorney, Agent, or Firm*—Davidson, Davidson & Kappel, LLC

(57) ABSTRACT

A stabilized solid controlled release dosage form having a coating derived from an aqueous dispersion of ethylcellulose is obtained by overcoating a substrate including a therapeutically active with an aqueous dispersion of ethylcellulose and then curing the coated substrate at a temperature and relative humidity elevated to a suitable level above ambient conditions until the coated dosage form attains a stabilized dissolution profile substantially unaffected by exposure to storage conditions of elevated temperature and/or elevated relative humidity.

31 Claims, No Drawings

STABILIZED CONTROLLED RELEASE SUBSTRATE HAVING A COATING DERIVED FROM AN AQUEOUS DISPERSION OF HYDROPHOBIC POLYMER

This application is a continuation of U.S. Ser. No. 08/899,924, filed Jul. 24, 1997, now U.S. Pat. No. 6,129,933, which is a divisional of U.S. Ser. No. 08/667,052, filed Jun. 20, 1996, now U.S. Pat. No. 5,681,585, which is a continuation-in-part of U.S. Ser. No. 08/561,829, filed Nov. 27, 1995, now U.S. Pat. No. 5,958,459, which is a continuation of U.S. Ser. No. 08/086,248, filed Jul. 1, 1993, abandoned, which is a continuation-in-part of U.S. Ser. No. 07/814,111, filed Dec. 24, 1991, now U.S. Pat. No. 5,273,760, the disclosures of which are herein incorporated by reference.

BACKGROUND OF THE INVENTION

It is the aim of all controlled release preparations to provide a longer duration of pharmacological response after the administration of the dosage form than is ordinarily experienced after the administration of an immediate release dosage form. Such extended periods of response provides for many inherent therapeutic benefits that are not achieved with short acting, immediate release products.

Controlled release formulations known in the art include specially coated beads or pellets, coated tablets and ion exchange resins, wherein the slow release of the active drug is brought about through selective breakdown of, or permeation through, the coating of the preparation or through formulation with a special matrix to affect the release of the drug.

An important aspect of all forms of controlled release dosage forms is related to the stability of the same. The stability of a pharmaceutical dosage form is related to maintaining its physical, chemical, microbiological, therapeutic, pharmaceutical, and toxicological properties when stored, i.e., in a particular container and environment. Stability study requirements are covered, e.g., in the Good Manufacturing Practices (GMPs), the U.S.P, as well as in New Drug Applications (NDAs) and Investigational New Drug Applications (INDs).

The ingredients used in sustained release dosage formulations often present special problems with regard to their physical stability during storage. For example, waxes which have been used in such formulations are known to undergo physical alterations on prolonged standing, thus precautions are taken to stabilize them at the time of manufacture or to prevent the change from occurring. Fats and waxy materials when used in purified states are known to crystallize in unstable forms, causing unpredictable variations in availability rates during stability testing at the time of manufacture and during later storage.

It is known that certain strategies can be undertaken to obtain stabilized controlled release formulations in many cases, such as insuring that the individual ingredients are in a stable form before they are incorporated into the product, and that processing does not change this condition, retarding the instability by including additional additives, and inducing the individual ingredients of the dosage form to reach a stable state before the product is finally completed.

It is also recognised that the moisture content of the product can also influence the stability of the product. Changes in the porosity and/or hydration level of a polymeric film, such as the ethyl celluloses, can alter the rate of water permeation and drug availability. Also, binders such as acacia are known to become less soluble when exposed to moisture and heat. Such problems have been handled by controls in the processing method and proper packaging of the product.

Hydrophobic polymers such as certain cellulose derivatives, zein, acrylic resins, waxes, higher aliphatic alcohols, and polylactic and polyglycolic acids have been used in the prior art to develop controlled release dosage forms. Methods of using these polymers to develop controlled release dosage forms such as tablets, capsules, suppositories, spheroids, beads or microspheres are to overcoat the individual dosage units with these hydrophobic polymers. It is known in the prior art that these hydrophobic coatings can be applied either from a solution, suspension or dry. Since most of these polymers have a low solubility in water, they are usually applied by dissolving the polymer in an organic solvent and spraying the solution onto the individual drug forms (such as beads or tablets) and evaporating off the solvent.

Aqueous dispersions of hydrophobic polymers have been used in the prior art to coat pharmaceutical dosage forms for aesthetic reasons such as film coating tablets or beads or for taste-making. However, these dosage forms are used for immediate release administration of the active drug contained in the dosage form.

The use of organic solvents in the preparation of polymer coatings is considered problematic as the formulations have inherent problems with regard to flammability, carcinogenicity, and safety in general. In addition, the use of organic solvents is disfavored due to environmental concerns.

Therefore, it is desirable to prepare a controlled release formulation prepared from an aqueous dispersion of a hydrophobic polymer. However, to date, attempts to prepare stable controlled release pharmaceutical formulations using aqueous dispersions of hydrophobic polymers have been unsuccessful due to stability problems. In particular, when coating these pharmaceutical forms using aqueous polymeric dispersions to obtain a desired release profile of the active drug(s) over several hours or longer, it is known in the art that the dissolution release profile changes on ageing. It is also known that this instability problem does not exist when the polymers are applied from organic solvent solution.

For example, Dressman, et al., Proceed. Intern. Symp. Control. Rel. Bioact. Mater., 18 (1991), pp. 654–655, Controlled Release Society, Inc. reported on tests conducted which showed that phenylpropanolamine HCl pellets coated with an ethyl cellulose-based film are only stable at room temperature under ambient humidity conditions. In these experiments, phenylpropanolamine HCl was overlaid on sugar seeds to a 76% loading, and coated with 10% ethyl cellulose applied from an aqueous dispersion. A second sample consisted of phenylpropanolamine spheronized with microcrystalline cellulose in a 70:30 ratio, then coated with 15% ethyl cellulose applied from an aqueous dispersion. Samples from each batch were stored for up to four weeks under conditions of room temperature/ambient humidity; room temperature/high humidity (75% RH); 37° C./ambient humidity; and 37° C./high humidity. The data for the dissolution profiles indicated that the lag time and percent drug released at 8 hours were unstable at all conditions other than room temperature/ambient humidity conditions.

Although the authors considered the pellets to be unaffected by storage conditions, they concluded that the release mechanism from the phenylpropanolamine HCl pellets overcoated with ethyl cellulose-based films appear to depend upon the pellet composition, and that under high relative humidity storage, the rate of release may be effected, especially if the samples were stored at elevated temperature.

Munday, et al., Drug Devel. and Indus. Phar., 17 (15) 2135–2143 (1991) report that film coated theophylline mini-tablets film coated with ethyl cellulose with PEG (2:1), and ethyl cellulose with Eudragit L (2:1) proved to have impeded dissolution upon storage under stress conditions, the degree of slowdown of release being said to be directly proportional to temperature, while the effect of relative humidity (RH) appeared to be insignificant.

The authors concluded therein that the decreased rate of release was due to the slowing in the rate of molecular diffusion of the drug across the polymeric coating material, and suggested that the change was due to significant alterations in the permeability of the polymer which occurred during the experimental storage.

Aqueous polymeric dispersions have been used to produce stable controlled release dosage forms, but this has only been possible by other methods such as incorporation of the same into the matrix of the dosage form, rather than via the use of a coating of the aqueous polymeric dispersion to obtain retardant properties.

OBJECTS AND SUMMARY OF THE INVENTION

It is therefore an object of the present invention to provide a controlled release dosage form for oral administration which comprises a coating of an aqueous dispersion of a hydrophobic polymer which is substantially stable despite exposure to elevated temperatures and/or elevated humidity levels during storage.

It is a further object of the present invention to provide a controlled release dosage form prepared with an overcoat of an aqueous dispersion of a hydrophobic polymer which is substantially stable under stress conditions, including even extended periods of high temperature and high humidity.

These objects and others have been accomplished by the present invention, which relates to a solid dosage form which has a controlled release overcoat derived from an aqueous dispersion of a hydrophobic polymer which provides a substantially stable release pattern of a therapeutically active agent(s) contained therein.

The present invention further relates to the surprising discovery that when the coated formulation is exposed to certain elevated or "stressed" conditions of temperature and humidity for a certain amount of time, a desired endpoint may be attained whereat the release rate of the therapeutically active agent does not substantially change upon ageing under a wide range of temperature and/or humidity conditions. This surprising discovery makes it possible to use aqueous dispersions of hydrophobic polymers for coating pharmaceutical dosage forms to produce stable controlled release pharmaceutical products.

The present invention is also related to a solid dosage form comprising a core comprising a therapeutically active agent and an overcoating derived from an aqueous dispersion of ethylcellulose in an amount sufficient to obtain a controlled release of the therapeutically active agent when the dosage form is exposed to aqueous solutions, e.g. gastric fluid. The solid dosage form is cured after the overcoating is applied such that the release of the therapeutically active agent is substantially unaffected by exposure to elevated temperature and/or humidity.

The present invention is also related to a stabilized controlled release solid dosage form for oral administration, comprising a plurality of inert pharmaceutically acceptable beads coated with a therapeutically active agent, and an ethylcellulose overcoat of a suitable thickness to obtain a controlled release of said therapeutically active agent when the solid dosage form is exposed to aqueous solution, the ethylcellulose overcoat being derived from an aqueous dispersion of ethylcellulose with an effective amount of a suitable plasticizing agent. The ethylcellulose coated beads are cured under stress conditions, i.e. at a temperature and relative humidity elevated to a suitable level above ambient conditions to attain a finished product which has a dissolution profile which is substantially unaffected by exposure to storage conditions of elevated temperature and/or humidity.

The present invention is further related to a stabilized solid controlled dosage form comprising a therapeutically active agent overcoated with an aqueous dispersion of ethylcellulose and cured at conditions of temperature and relative humidity greater than ambient conditions until a stabilized dissolution profile substantially unaffected by exposure to storage conditions of elevated temperature and/or elevated relative humidity is obtained.

The present invention is also related to a method for obtaining a stabilized controlled release formulation comprising a substrate coated with an aqueous dispersion of a hydrophobic polymer, comprising preparing an aqueous dispersion of ethycellulose, preparing a substrate comprising a therapeutically active agent, overcoating the substrate with a sufficient amount of the aqueous dispersion of ethycellulose to obtain a predetermined controlled release of the therapeutically active agent when the coated particles are exposed to aqueous solutions, and curing the coated substrate under stressed conditions by subjecting said coated particles to greater than ambient temperature and humidity and continuing the curing until an endpoint is reached at which the coated substrate attains a dissolution profile which is substantially unaffected by exposure to storage conditions of elevated temperature and/or humidity.

In a further embodiment, the method further includes the step of determining the endpoint for a particular formulation by exposing the formulation to various stages of the above-mentioned curing and obtaining dissolution profiles for the formulation until the dissolution profiles of the formulation are substantially stabilized. The formulation is then modified, if necessary, to obtain a desired dissolution profile of the therapeutically active agent based on the end point.

DETAILED DESCRIPTION

Ethylcellulose, which is a cellulose ether that is formed by the reaction of ethyl chloride with alkaline cellulose, is completely insoluble in water and gastrointestinal juices, and therefore to date has been considered not to be suitable by itself for tablet coating. It has, however, been commonly used in combination with hydroxypropyl methylcellulose and other film-formers to toughen or influence the dissolution rate of the film. Due to the solubility characteristics of ethylcellulose, this polymer has been mainly applied to the above-mentioned formulations from organic solutions.

Many polymers have been investigated for use in film-coating. Most film-coats are prepared by deposition of one or more film-forming polymers resulting in coats that usually represent no more than about 2–5% by weight of the final coated product. The film-coating has been used in conjunction with the preparation of tablets, pills, capsules, granules, and powders. The characteristics of the polymer used in the film-coating is governed by the structure, size and properties of its macromolecules. Common film-formers used in pharmaceuticals as nonenteric materials include hydroxypropyl methylcellulose, methyl hydroxyethylcellulose, hydroxypropylcellulose, sodium carboxymethylcellulose, ethylcellulose, and others.

In order to obtain a controlled release formulation, it is usually necessary to overcoat the substrate comprising the therapeutically active agent with a sufficient amount of the aqueous dispersion of ethylcellulose to obtain a weight gain level from about 5 to about 15 percent, although the overcoat may be lesser or greater depending upon the physical properties of the therapeutically active agent and the desired release rate, the inclusion of plasticizer in the aqueous dispersion of ethylcellulose and the manner of incorporation of the same, for example.

An example of a suitable controlled release formulation pursuant to the present invention will provide a dissolution rate in vitro of the dosage form, when measured by the USP Paddle Method at 100 rpm in 900 ml aqueous buffer (pH between 1.6 and 7.2) at 37° C., is between 12.5 and 42.5% (by wt) therapeutically active agent released after 1 hour, between 25 and 55% (by wt) released after 2 hours, between 45 and 75% (by wt) released after 4 hours and between 55 and 85% (by wt) released after 6 hours. This example is, of course, not intended to be limiting in any manner whatsoever.

The aqueous dispersions of hydrophobic polymers used as coatings in the present invention may be used in conjunction with tablets, spheroids (or beads), microspheres, seeds, pellets, ion-exchange resin beads, and other multiparticulate systems in order to obtain a desired controlled release of the therapeutically active agent. Granules, spheroids, or pellets, etc., prepared in accordance with the present invention can be presented in a capsule or in any other suitable dosage form.

Because ethylcellulose has a relatively high glass transition temperature and does not form flexible films under normal coating conditions, it is necessary to plasticize the ethylcellulose before using the same as a coating material.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

With respect to handling and storage conditions, FMC states that Aquacoat® will undergo a rise in viscosity upon prolonged exposure to temperatures below 15° C. or above 35° C., and that viscosity can be reduced to less than 100 cps by applying shear (e.g., propeller type mixer). FMC further states that a continuous film may be formed through a process known as gradual coalescence wherein the individual latex particles coalesce to form a continuous film of plasticized ethylcellulose polymer. After this period, the properties are said to remain constant. Higher coating temperatures, or a high temperature "curing" step is said by FMC to accelerate the process. If the coalescence process is not complete, FMC states that variability in release rates will result.

However, as will be demonstrated by the examples provided herein, it has been found that curing the film coating simply by utilizing a higher coating temperature or a high temperature curing step will not effectively stabilize the dissolution profile of the product upon storing.

Another aqueous dispersion of ethylcellulose is commerically available as Surelease® (Colorcon, Inc., West Point, Pa., U.S.A). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

The coating formulations of the present invention should be capable of producing a strong, continuous film that is smooth and elegant, capable of supporting pigments and other coating additives, non-toxic, inert, and tack-free.

It is preferred that the aqueous dispersion of ethylcellulose used in the present invention include an effective amount of a suitable plasticizing agent, as it has been found that the use of a plasticizer will further improve the physical properties of the film. The plasticization of the ethylcellulose may be accomplished either by so-called "internal plasticization" and "external plasticization."

Internal plasticization usually pertains directly to molecular modifications of the polymer during its manufacture, e.g., by copolymerization, such as altering and/or substituting functional groups, controlling the number of side chains, or controlling the length of the polymer. Such techniques are usually not performed by the formulator of the coating solution.

External plasticization involves the addition of a material to a film solution so that the requisite changes in film properties of the dry film can be achieved.

The suitability of a plasticizer depends on its affinity or solvating power for the polymer and its effectiveness at interfering with polymer—polymer attachments. Such activity imparts the desired flexibility by relieving molecular rigidity. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

An important parameter in the determination of a suitable plasticizer for a polymer is related to the glass transition temperature (Tg) of the polymer. The glass transition temperature is related to the temperature or temperature range where there is a fundamental change in the physical properties of the polymer. This change does not reflect a change in state, but rather a change in the macromolecular mobility of the polymer.

Below the Tg, the polymer chain mobility is severely restricted. Thus, for a given polymer, if its Tg is above room temperature, the polymer will behave as a glass, being hard, non-pliable and rather brittle, properties which could be somewhat restrictive in film coating since the coated dosage form may be subjected to a certain amount of external stress.

Incorporation of suitable plasticizers into the polymer matrix effectively reduces the Tg, so that under ambient conditions the films are softer, more pliable and often stronger, and thus better able to resist mechanical stress.

Other aspects of suitable plasticizers include the ability of the plasticizer to act as a good "swelling agent" for the ethylcellulose, and the insolubility of the plasticizer in water.

Examples of suitable plasticizers include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

The stabilized controlled release formulations of the present invention slowly release the therapeutically active agent, e.g., when ingested and exposed to gastric fluids, and then to intestinal fluids. The controlled release profile of the formulations of the invention can be altered, for example, by varying the amount of overcoating with the aqueous dispersion of ethylcellulose, altering the manner in which the plasticizer is added to the aqueous dispersion of ethylcellulose, by varying the amount of plasticizer relative to ethylcellulose, by the inclusion of additional ingredients or excipients, by altering the methods of manufacture, etc.

A wide variety of therapeutically active agents can be used in conjunction with the present invention. The therapeutically active agents (e.g. pharamaceutical agents) which may be used in the compositions of the present invention include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), anti-inflammatory agents (e.g., naproxyn, diclofenac, indomethacin, ibuprofen, acetaminophen, aspirin, sulindac), gastro-intestinals and anti-emetics (e.g., metoclopramide), anti-epileptics (e.g., phenytoin, meprobamate and nitrezepam), vasodilators (e.g., nifedipine, papaverine, diltiazem and nicardirine), anti-tussive agents and expectorants (e.g., codeine phosphate), anti-asthmatics (e.g. theophylline), anti-spasmodics (e.g. atropine, scopolamine), hormones (e.g., insulin, leparin), diuretics (e.g., eltacrymic acid, bendrofluazide), anti-hypotensives (e.g., propranolol, clonidine), bronchodilators (e.g., albuterol), anti-inflammatory steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, antacids, vitamins, stimulants (including appetite suppressants such as phenylpropanolamine). The above list is not meant to be exclusive.

In certain preferrred embodiments, the therapeutically active agent comprises hydromorphone, oxycodone, dihydrocodeine, codeine, dihydromorphine, morphine, buprenorphine, salts or any of the foregoing, and mixtures of any of the foregoing, and the like.

When the aqueous dispersion of ethycellulose is used to coat inert pharmaceutical beads such as nu pariel 18/20 beads, a plurality of the resultant stabilized solid controlled release beads may thereafter be placed in a gelatin capsule in an amount sufficient to provide an effective controlled release dose when ingested and contacted by gastric fluid. In this embodiment, beads coated with a therapeutically active agent are prepared, e.g. by dissolving the therapeutically active agent in water and then spraying the solution onto a substrate, for example, nu pariel 18/20 beads, using a Wurster insert. Optionally, additional ingredients are also added prior to coating the beads in order to assist the hydromorphone binding to the beads, and/or to color the solution, etc. For example, a product which includes hydroxypropyl methylcellulose, etc. with or without colorant may be added to the solution and the solution mixed (e.g., for about 1 hour) prior to application of the same onto the beads. The resultant coated substrate, in this example beads, may then be optionally overcoated with a barrier agent, to separate the therapeuticaly active agent from the ethylcellulose coating. An example of a suitable barrier agent is one which comprises hydroxypropyl methylcellulose. However, any film-former known in the art may be used. It is preferred that the barrier agent does not affect the dissolution rate of the final product.

The hydromorphone, HPMC protected (optional) beads may then be overcoated with an aqueous dispersion of ethylcellulose. The aqueous dispersion of ethylcellulose preferably further includes an effective amount of plasticizer, e.g., triethyl citrate. Pre-formulated aqueous dispersions of ethylcellulose, such as Aquacoat® or Surelease®, may be used. If Surelease® is used, it is not necessary to separately add a plasticizer.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of ethylcellulose. For example, color be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used.

The plasticized aqueous dispersion of ethylcellulose may be applied onto the substrate comprising the therapeutically active agent by spraying using any suitable spray equipment known in the art. A sufficient amount of the aqueous dispersion of ethylcellulose to obtain a predetermined controlled release of said therapeutically active agent when said coated substrate is exposed to aqueous solutions, e.g. gastric fluid, is preferably applied, taking into account the physically characteristics of the therapeutically active agent, the manner of incorporation of the plasticizer, etc. After coating with Aquacoat®, a further overcoat of a film-former, such as Opadry®, is optionally applied to the beads. This overcoat is provided, if at all, in order to substantially reduce agglomeration of the beads.

Next, the coated beads are cured in order to obtain a stablized release rate of the therapeutically active agent. Curing is traditionally carried out, if at all, via a forced-air oven at 60° C. for anywhere from 2–24 hours. This standard curing does not stabilize the dissolution profile of the formulation, as will be demonstrated by the examples set forth herein.

The curing step pursuant to the present invention is accomplished by subjecting the coated beads to "stressed conditions" by subjecting said coated substrate to greater than normal, ambient (i.e., room) temperature and relative humidity and continuing the curing until an endpoint is reached at which the coated beads attain a dissolution profile which is substantially unaffected by further exposure to storage conditions of elevated temperature and/or humidity. More particularly, the coated substrates of the present invention should be cured at a temperature greater than the glass transition temperature of the coating solution (i.e., ethylcellulose) and at a greater than ambient humidity.

One possible mechanism for the change in the dissolution profile of prior art products cured by the standard methods, i.e. curing for 2 hours or more at 60° C. dry heat, is that these products continue to cure during storage, and may never reach a stabilized end-point at which the product provides a substantially constant dissolution profile. In contrast, the cured products of the present invention provide a release rate of the therapeutically active agent which is substantially unaffected during storage by elevations in temperature and humidity.

In preferred embodiments of the present invention, the stabilized product is obtained by subjecting the coated substrate to oven curing at elevated temperature/humidity levels for the required time period, the optimum values for temperature, humidity and time for the particular formulation being determined experimentally.

In certain embodiments of the present invention, the stabilized product is obtained via an oven curing conducted at a temperature of about 60° C. and a relative humidity from about 60% to about 100% for a time period from about 48 to about 72 hours. This is the case for the hydromorphone beads described in the examples provided below. However, one skilled in the art will recognize that necessary curing conditions may be changed somewhat, and may in fact be broader than the above-mentioned temperature, humidity and time ranges, depending upon the particular formulation, in order to obtain a stabilized product.

When the controlled release coating of the present invention is to be applied to tablets, the tablet core (e.g. the substrate) may comprise the active agent along with any pharmaceutically accepted inert pharmaceutical filler (diluent) material, including but not limited to sucrose, dextrose, lactose, microcrystalline cellulose, xylitol, fructose, sorbitol, mixtures thereof and the like. Also, an effective amount of any generally accepted pharmaceutical lubricant, including the calcium or magnesium soaps may be added to the above-mentioned ingredients of the excipient prior to compression of the tablet core ingredients. Most preferred is magnesium stearate in an amount of about 0.5–3% by weight of the solid dosage form.

Tablets overcoated with a sufficient amount of aqueous dispersions of ethylcellulose to achieve a controlled release formulation pursuant to the present may be prepared and cured in similar fashion as explained above with regard to the preparation of beads. One skilled in the art will recognize that necessary curing conditions with regard to the particular elevated temperature, elevated humidity and time ranges necessary to obtain a stabilized product, will depend upon the particular formulation.

DETAILED DESCRIPTION OF THE PREFERRED EMBODIMENTS

The following examples illustrate various aspects of the present invention. They are not to be construed to limit the claims in any manner whatsoever.

EXAMPLE 1

Hydromorphone beads were prepared by dissolving hydromorphone HCl in water, adding Opadry® Y-5-1442, light pink (a product commercially available from Coloron, West Point, Pa., which contains hydroxypropyl methylcellulose, hydroxypropyl cellulose, titanium dioxide, polyethylene glycol and D&C Red No. 30 Aluminum Lake), 20% w/w, and mixing for about 1 hour, and then spraying onto nu pariel 18/20 beads using a Wurster insert. The resultant coated beads were then overcoated with Opadry® Y-5-1442 light pink (15% w/w). The resultant preparation had the formula set forth in Table 1 below:

TABLE 1

| Ingredient | Percent | Amt/Unit |
|---|---|---|
| Hydromorphone HCl | 4.75% | 4 mg |
| NU Pariel 18/20 | 87.9% | 74 mg |
| opadry ® Lt. Pink Y-5-1442 | 2.4% | 2 mg |
| opadry ® " (overcoat) | 5.0% | 4.2 mg |
| | 100.0% | 84.2 mg |

The hydromorphone, HPMC protected beads were then overcoated with 15% w/w Aquacoat® (including triethyl citrate), and then overcoated with Opadry® Light Pink 5% w/w after curing (see Table 2). The beads cured at high humidity were dried in a fluid bed before the final overcoat.

TABLE 2

| Composition After Coating | |
|---|---|
| Ingredient | Percent |
| Hydromorphone beads | 80.57% |
| Aquacoat ® ECD 30 | 12.06% |
| Triethyl citrate | 2.39% |
| Opadry ® Lt. Pink | 4.98% |
| Y-5-1442 (Overcoat) | 100.0% |

The product was then divided into four portions. In Example 1, the coated beads were placed in a 30 cc amber glass vial and cured in an oven for 72 hours at 60° C./85% relative humidity. In Comparative Example 1A, the coated beads were cured for 24 hours at 60° C. under dry conditions. In Comparative Example 1B, the coated beads were cured for 72 hours at 60° C. under dry conditions. In Comparative Example 1C, the coated beads were cured for 24 hours at 60° C. at 85% relative humidity.

All products cured at the four above-mentioned different conditions were then tested for stability under the following conditions: Room Temperature; 37° C. dry; 37° C./80% Relative Humidity (RH); 50° C. dry; 60° C. dry; and 60° C./85% RH.

The relative humidity in a water-filled desiccator in a 60° C. oven was determined as follows. First, about 500 grams of purified water is poured into a plastic desiccator and the metal guard inserted. A hygrometer/temperature indicator is placed on top of the guard and the desiccator covered and placed in the 60° C. oven for 24 hours. After 24 hours the relative humidity in the desiccator was 85% while the temperature was still 60° C. On placing the hygrometer alone in the 60° C. oven for 24 hours, the relative humidity was 9% at 60° C.

The dissolution tests were carried out via the USP Basket Method, 37° C., 100 RPM, first hour 700 ml gastric fluid at pH 1.2, then changed to 900 ml at 7.5. In each instance, the dissolution was conducted by placing an open capsule containing the specified amount of cured beads (8 mg hydromorphone HCl, 209 mg beads±10%) into a vessel.

It was observed that the dissolution of Example 1 did not change under these accelerated conditions, except that changes were seen with respect to the extreme conditions of 60° C./85% RH. The results for Example 1 are set forth in Tables 3–8 below, :

TABLE 3

ROOM TEMPERATURE

| Time (wks) | Hydromorphone HCl (Amount) | Dissolution | | | | | | |
|---|---|---|---|---|---|---|---|---|
| | | 1 | 2 | 3 | 8 | 12 | 18 | 24 |
| Initial | 8.14 mg | 0 | 4.6 | 29.5 | 52.6 | 64.7 | 76.6 | 82.8 |
| 1 | 7.95 mg | 0 | 5.1 | 30.3 | 55.0 | 67.4 | 79.8 | 88.9 |
| 4 | 7.80 mg | 1.3 | 8.2 | 33.5 | 57.4 | 70.0 | 82.8 | 90.9 |
| 8 | 7.78 mg | 0.7 | 6.0 | 30.5 | 54.0 | 66.4 | 78.0 | 88.2 |

TABLE 4

37° C. DRY

| Time (wks) | Hydromorphone HCl (Amount) | Dissolution | | | | | | |
|---|---|---|---|---|---|---|---|---|
| | | 1 | 2 | 3 | 8 | 12 | 18 | 24 |
| Initial | 8.14 mg | 0 | 4.6 | 29.5 | 52.6 | 64.7 | 76.6 | 82.8 |
| 1 | 7.96 mg | 0 | 6.0 | 30.8 | 55.3 | 68.0 | 81.6 | 89.7 |
| 4 | 7.91 mg | 2 | 8.1 | 33.2 | 56.6 | 70.2 | 82.0 | 91.3 |
| 8 | 7.73 mg | 1 | 5.8 | 31.3 | 57.5 | 64.6 | 82.7 | 91.6 |

TABLE 5

37° C./80% RH

| Time (wks) | Hydromorphone HCl (Amount) | Dissolution | | | | | | |
|---|---|---|---|---|---|---|---|---|
| | | 1 | 2 | 3 | 8 | 12 | 18 | 24 |
| Initial | 8.19 mg | 0 | 4.6 | 29.5 | 52.6 | 64.7 | 76.6 | 82.8 |
| 1 | 7.85 mg | 0 | 5.6 | 31.0 | 55.1 | 68.5 | 80.3 | 89.1 |
| 4 | 8.16 mg | 2.4 | 7.6 | 32.3 | 52.8 | 64.4 | 75.4 | 82.7 |
| 8 | 8.22 mg | 2.9 | 7.9 | 33.5 | 53.3 | 64.5 | 73.6 | 81.3 |

TABLE 6

50° C. (dry)

| Time (wks) | Hydromorphone HCl (Amount) | Dissolution | | | | | | |
|---|---|---|---|---|---|---|---|---|
| | | 1 | 2 | 3 | 8 | 12 | 18 | 24 |
| Initial | 8.14 mg | 0 | 4.6 | 29.5 | 52.6 | 64.7 | 76.6 | 82.8 |
| 1 | 8.14 mg | 0 | 6.3 | 32.7 | 56.3 | 68.3 | 80.8 | 89 |
| 4 | 7.81 mg | 2.3 | 10 | 37.0 | 59.6 | 72.0 | 84.5 | 92 |
| 8 | 7.74 mg | 2 | 10.4 | 35.8 | 59.2 | 71.3 | 82.3 | 90.5 |

TABLE 7

60° C. (dry)

| Time (wks) | Hydromorphone HCl (Amount) | Dissolution | | | | | | |
|---|---|---|---|---|---|---|---|---|
| | | 1 | 2 | 3 | 8 | 12 | 18 | 24 |
| Initial | 8.14 mg | 0 | 4.6 | 29.5 | 52.6 | 64.7 | 76.6 | 82.8 |
| 1 | 8.13 mg | 0 | 6.7 | 34.6 | 57.8 | 70.3 | 82.1 | 90.5 |
| 4 | 8.30 mg | 2.7 | 10.6 | 36.6 | 56.8 | 68.7 | 80.4 | 85.6 |
| 8 | 7.94 mg | 3.6 | 11.9 | 37.4 | 58.4 | 71.1 | 80.6 | 89.3 |

TABLE 8

60° C./100% RH

| Time (wks) | Hydromorphone HCl (Amount) | Dissolution | | | | | | |
|---|---|---|---|---|---|---|---|---|
| | | 1 | 2 | 3 | 8 | 12 | 18 | 24 |
| Initial | 8.14 mg | 0 | 4.6 | 29.5 | 52.6 | 64.7 | 76.6 | 82.8 |
| 1 | 7.26 mg | 6.1 | 9.9 | 23.4 | 42.4 | 53.3 | 63.1 | 72.5 |
| 4 | 6.64 mg | 19 | 23.7 | 32.5 | 41.4 | 46.7 | 53.0 | 51.7 |
| 8 | 5.38 mg | 25.1 | 28.4 | 33.2 | 40.0 | 44.1 | 47.7 | 52.0 |

In contrast, the dissolution profiles of Comparative Examples 1A, 1B and 1C continued to slow down (e.g., cure) at all accelerated conditions. The results are set forth in Tables 9, 10 and 11, respectively.

TABLE 9

Comparative Example 1A

| Conditions/ Time | Hydromorphone HCl (Amount) | Dissolution | | | | | | |
|---|---|---|---|---|---|---|---|---|
| | | 1 | 2 | 3 | 8 | 12 | 18 | 24 |
| Initial Room Temp. | 9.03 mg | 17.8 | 43.6 | 63.6 | 78.8 | 86.7 | 94.7 | 94.2 |
| 8 wks 37° C. (dry) | 8.79 mg | 18.4 | 35.9 | 58.2 | 76.3 | 88.7 | 97 | * |
| 8 wks | 8.50 mg | 14 | 36.5 | 59.1 | 81.1 | 91.4 | 99.4 | * |

TABLE 9-continued

Comparative Example 1A

| Conditions/<br>Time | Hydromorphone<br>HCl<br>(Amount) | Dissolution | | | | | | |
|---|---|---|---|---|---|---|---|---|
| | | 1 | 2 | 3 | 8 | 12 | 18 | 24 |
| 37° C./80% RH | | | | | | | | |
| 8 wks | 8.15 mg | 6.6 | 23.6 | 41.2 | 60.7 | 72.3 | 83.1 | * |
| 50° C. (dry) | | | | | | | | |
| 8 wks | 8.45 mg | 17.3 | 36 | 56.1 | 78.1 | 89.1 | 97.1 | 102.6 |
| 60° C. (dry) | | | | | | | | |
| 8 wks | 8.65 mg | 7.3 | 28.5 | 48.9 | 64.4 | 82 | 92.3 | 99.1 |
| 60° C./100% RH | | | | | | | | |
| 8 wks | 5.81 mg | 17.5 | 22.6 | 28.8 | 36.5 | 41.7 | 46.5 | 50.3 |

TABLE 10

Comparative Example 1B

| Conditions/<br>Time | Hydromorphone<br>HCl<br>(Amount) | Dissolution | | | | | | |
|---|---|---|---|---|---|---|---|---|
| | | 1 | 2 | 3 | 8 | 12 | 18 | 24 |
| Initial<br>Room Temp. | 8.82 mg | 4.7 | 35.5 | 58.3 | 75.6 | 87.3 | 96.0 | 98.2 |
| 8 wks<br>37° C. (dry) | 8.29 mg | 8.7 | 34.6 | 59.3 | 80.8 | 92.1 | 99.2 | 105.7 |
| 8 wks<br>37° C./80% RH | 8.34 mg | 8.3 | 36.1 | 55.9 | 77.4 | 87.3 | 97.8 | 103.1 |
| 8 wks<br>50° C. (dry) | 8.86 mg | 4.9 | 25.4 | 43.6 | 61.7 | 70 | 80 | 87.2 |
| 8 wks<br>60° C. (dry) | 8.71 mg | 10.8 | 35.4 | 55.9 | 77.2 | 88.9 | 99.5 | 103.2 |
| 8 wks<br>60° C./100% RH | 8.30 mg | 5.3 | 32 | 54.1 | 76.6 | 87.2 | 99.8 | 105.5 |
| 8 wks | 6.22 mg | 16.3 | 21.2 | 27.4 | 35.9 | 40.5 | 46.2 | 49.4 |

TABLE 11

Comparative Example 1C

| Conditions/<br>Time | Hydromorphone<br>HCl<br>(Amount) | Dissolution | | | | | | |
|---|---|---|---|---|---|---|---|---|
| | | 1 | 2 | 3 | 8 | 12 | 18 | 24 |
| Initial<br>Room Temp. | 8.71 mg | 0.7 | 15.3 | 41.9 | 60.7 | 71.2 | 82.4 | 86.7 |
| 8 wks<br>37° C. (dry) | 8.40 mg | 1 | 14.2 | 39.8 | 58.8 | 69.1 | 79.1 | 87.2 |
| 8 wks<br>37° C./80% RH | 8.84 mg | 2.7 | 14.5 | 40.5 | 60.4 | 71 | 81.3 | 89.8 |
| 8 wks<br>50° C. (dry) | 8.78 mg | 2.5 | 12.4 | 37.8 | 54.6 | 63.8 | 73.3 | * |
| 8 wks | 8.71 mg | 3.2 | 17.5 | 42.3 | 61.1 | 70.8 | 81 | 87.9 |

TABLE 11-continued

Comparative Example 1C

| Conditions/ Time | Hydromorphone HCl (Amount) | Dissolution | | | | | | |
|---|---|---|---|---|---|---|---|---|
| | | 1 | 2 | 3 | 8 | 12 | 18 | 24 |
| 60° C. (dry) | | | | | | | | |
| 8 wks | 8.57 mg | 2.9 | 18.2 | 43.4 | 62.5 | 73.6 | 84.3 | * |
| 60° C./100% RH | | | | | | | | |
| 8 wks | 6.10 mg | 15.7 | 20.3 | 26.4 | 33.8 | 38.3 | 43.1 | 46.7 |

FIG. 1 is a graphical representation of the dissolution results obtained with Example 1, comparing the initial dissolution profile with the dissolution profile after 8 weeks storage at 37° C./80% RH.

FIG. 2 is a graphical representation of the dissolution profile of Comparative Example 1A, comparing the initial dissolution profile with the dissolution profile after 8 weeks storage at 37° C./80% RH.

FIG. 3 is a graphical representation of the dissolution profile of Comparative Example 1B, comparing the initial dissolution profile with the dissolution profile after 8 weeks storage at 37° C./80% RH.

FIG. 4 is a graphical representation of the dissolution profile of Comparative Example 1C, comparing the initial dissolution profile with the dissolution profile after 8 weeks storage at 37° C./80% RH.

Comparing the results depicted in FIG. 1 (Example 1) with the results depicted in FIGS. 2–4 (the comparative examples), it is readily apparent that only in Example 1 were the initial and 8 week dissolution profiles substantially identical under storage conditions of 37° C./80% RH.

FIG. 5 is a graphical representation of the dissolution profiles of Example 1, comparing the initial dissolution profile with the dissolution profiles obtained after 8 weeks storage under various conditions (room temperature; 37° C./80% RH; and 60° C. dry). The dissolution profiles of Example 1 after 8 weeks under these various conditions is seen to be substantially identical.

Finally, FIG. 6 is a graphical representation of the initial dissolution profiles obtained after various curing conditions (curing of 2 hrs at 60° C. dry (the prior art); 72 hrs at 60° C./85% RH (Comparative Example 1); 24 hrs at 60° C./85% RH (Comparative Example 1A); 24 hrs at 60° C. dry (Comparative Example 1B); and 72 hrs at 60° C. dry (Comparative Example 1C)).

Example 2—Curing at 60° C. Dry Heat—Longer Drying

In Example 2, hydromorphone HCl beads were prepared in accordance with Example 1 in order to determine if the stabilized initial dissolution achieved after curing at 60° C./85% RH could instead be achieved by a longer drying period without humidity. After coating with Aquacoat®, a further overcoat of Opadry® Y-5-1442, light pink is applied to the beads. The coated product had the composition set forth in Table 12 below:

TABLE 12

Composition After Coating

| Ingredient | Percent | Amt/Unit |
|---|---|---|
| Hydromorphone beads | 80.57% | 84.2 mg |
| Aquacoat ® ECD 30 | 12.06% | 12.6 mg |
| Triethyl citrate | 2.39% | 2.5 mg |
| Opadry ® Lt. Pink (Overcoat) | 4.98% | 5.2 mg |
| | 100.0% | 99.3 mg |

The Aquacoat® coated hydromorphone HCl beads were then cured in a 60° C. dry oven, and stored at 60° dry heat. The cured beads were placed in open gelatin capsules containing the specified amount of cured beads (about 8 mg hydromorphone HCl), and dissolution studies were then conducted in the manner set forth in Example 1 on three samples at the following time points: initial, 1 day, 2 days, 7 days, and 21 days in order to determine the stability of the dissolution profile. Dissolution studies were conducted as detailed above on the three samples. The mean results are set forth in Table 13 below:

TABLE 13

| Time (Days) | Wt (mg) | Dissolution (Time) | | | | | | |
|---|---|---|---|---|---|---|---|---|
| | | 1 hr | 2 hr | 4 hr | 8 hr | 12 hrs | 18 hrs | 24 hrs |
| Initial | 196.7 | 15.6 | 43.8 | 68.7 | 89.9 | 101.0 | 109.2 | 113.8 |
| 1 | 196.3 | 3.7 | 37.5 | 63.5 | 84.9 | 97.5 | 107.2 | 112.3 |
| 2 | 196.3 | 4.8 | 37.0 | 62.9 | 84.8 | 95.1 | 104.7 | 111.8 |
| 7 | 197.3 | 13.5 | 37.8 | 63.3 | 84.9 | 98.8 | 108.6 | 115.9 |
| 21 | 197.3 | 17.4 | 36.5 | 58.4 | 77.9 | 88.9 | 98.2 | 103.1 |

From the results set forth in Table 13 above, it is apparent that a profound slow down in release rate of the samples of Example 2 occurred, as compared with the high temperature/high humidity condition of Example 1. In other words, an endpoint was not reached at which the dissolution profile gets down to the base level of Example 1.

Example 3—Increased Mixing Time

In Example 3, another attempt to stabilize Aquacoat® coated hydromorphone HCl beads using the premise that high temperature is not enough to insure complete coalescence of the ethylcellulose film. Normal time of mixing (and bonding) plasticizer and Aquacoat® is recommended by FMC to be 30 minutes. In Example 3, the contact time of the plasticizer (triethyl citrate) with the ethylcellulose polymer dispersion (Aquacoat®) was increased to 24 hours.

The coated beads were prepared in accordance with Example 1 and then placed in a 30 cc amber glass vial and cured in a 60° C. dry oven. Dissolution studies were then conducted on three samples at the following time points: 1 day, 2 days, 7 days and 11 days. Mean results are set forth in Table 14 below:

TABLE 14

| Time (Days) | Wt (mg) | Dissolution (Time) | | | | | | |
|---|---|---|---|---|---|---|---|---|
| | | 1 hr | 2 hr | 4 hr | 8 hr | 12 hrs | 18 hrs | 24 hrs |
| 1 | 210.7 | 27.7 | 53.3 | 77.3 | 95.7 | 103.4 | 108.2 | 110.4 |
| 2 | 209.7 | 25.9 | 50.3 | 74.3 | 94.2 | 101.9 | 106.4 | 110.2 |
| 7 | 209.7 | 24.8 | 48.3 | 73.1 | 95.2 | 102.7 | 108.5 | 112.6 |
| 11 | 210.3 | 24.0 | 45.4 | 70.5 | 94.9 | 103.9 | 113.3 | 115.9 |

From the results set forth in Table 14 above, it is apparent that a profound slow down in release rate of the samples of Example 2 occurred, as compared with the high temperature/high humidity condition of Example 1. In other words, an endpoint was not reached at which the dissolution profile gets down to the base level of Example 1.

Example 4—Recommended Curing (Prior Art)

Hydromorphone beads were prepared by dissolving hydromorphone HCl in water, adding Opadry®, and mixing for about 1 hour, and then spraying onto nu pariel 18/20 beads using a Wurster insert. The resultant coated beads were then overcoated with Opadry® Y-5-1442 light pink (15% w/w). The beads were then overcoated with a aqueous dispersion of Aquacoat® to a 15% weight gain according to Table 15 below:

TABLE 15

| Ingredient | Percent (wt) | Amt/Unit |
|---|---|---|
| Hydromorphone beads | 84.7 | 80 mg |
| Aquacoat ® CD 30 | 12.7 | 12 mg |
| Citroflex ® 2A (Triethylcitrate) | 2.5 | 2.4 mg |
| | 99.9 | 94.4 mg |

After the resin was applied to the beads, the beads were cured in a fluid bed for about 2 hours at 60° C., as suggested in the literature and as recommended by FMC, since it is above the Tg for Aquacoat® plasticized with triethyl citrate at 20% level of solids.

The cured beads were then stored at room temperature, with dissolution studies being conducted initially and at 3 months. Samples were also stored at 37° C./80% RH. The mean results are provided in Table 16:

TABLE 16

| Time | Mean wt | 1 hr | 2 hr | 4 hr | 8 hr | 12 hrs | 18 hrs | 24 hrs |
|---|---|---|---|---|---|---|---|---|
| Initial | 283.2 | 30.4 | 44 | 70.2 | 89.1 | 97.0 | 101.3 | 102.1 |
| 3 mos 37° C./80% RH | 282.3 | 36.2 | 57.8 | 76.9 | 89.0 | 93.4 | 96.6 | 98.5 |
| 1 mo | 288.4 | 0.5 | 26.7 | 50.5 | 69.6 | 80.7 | 90.7 | 97.0 |
| 2 mos | 287.3 | 0.6 | 25.1 | 50.7 | 70.3 | 81.6 | 92.2 | 98.8 |
| 3 mos | 293.7 | 1.2 | 23.7 | 48.6 | 65.6 | 74.5 | 80.2 | 83.5 |

From the results provided in Table 16 above, it can be seen that the dissolution profile of the samples stored at room temperature were acceptable. However, the dissolution of the samples slowed dramatically when stored at 37° C./80% RH.

Samples from the batch of Example 4 were repackaged, stored and thereafter subjected to heat under dry conditions at 37° C. and moisture (37° C./80% RH). The dissolution results are provided in Table 17 below:

TABLE 17

| Time | Mean wt | 1 hr | 2 hr | 4 hr | 8 hr | 12 hrs | 18 hrs | 24 hrs |
|---|---|---|---|---|---|---|---|---|
| Initial | 283.2 | 30.4 | 49.0 | 70.3 | 89.1 | 97.0 | 101.3 | 102.1 |
| 37° Dry | | | | | | | | |
| 2 wks | 283.2 | 25.0 | 44.4 | 65.0 | 84.5 | 92.9 | 100.7 | 104.4 |
| 4 wks | 280.7 | 21.5 | 28.0 | 63.5 | 84.3 | 95.6 | — | — |
| 37° C./80% RH | | | | | | | | |
| 2 wks | 283.2 | 16.6 | 39.1 | 60.5 | 80.1 | 89.8 | 99.8 | 103.4 |
| 4 wks | 281.3 | 4.6 | 26.6 | 53.7 | 71.4 | 82.1 | — | — |

From the results set forth above, it is apparent that under dry conditions at 37° C., the dissolution of Example 4 did not come to the same endpoint as at 37° C./80% RH. Thus, the combination of both moisture and heat was required to complete the curing.

Examples 5–7

To test the effectiveness of high temperature (60° C.), high humidity curing as an effective process of stabilizing plasticized ethylcellulose controlled release films, Examples 5–7 were manufactured at different levels of Aquacoat® load.

In each of Examples 5–7, hydromorphone beads were made according to Example 1. Thereafter, overcoating of 5% w/w, 10% w/w, and 15% w/w were applied to Examples 5–7 respectively, according to the formulas set forth in Tables 18–20:

TABLE 18

Composition of EX. 5 After Coating

| Ingredient | Percent | Amt/Unit |
|---|---|---|
| Hydromorphone beads | 84.2% | 84.2 mg |
| Aquacoat ® ECD 30 | 4.7% | 4.2 mg |
| Triethyl citrate | 0.9% | 0.84 mg |
| | 100% | 89.24 mg |

TABLE 19

Composition of Ex. 6 After Coating

| Ingredient | Percent | Amt/Unit |
|---|---|---|
| Hydromorphone beads | 89.3% | 84.2 mg |
| Aquacoat ® ECD 30 | 8.9% | 8.4 mg |
| Triethyl citrate | 1.8% | 1.7 mg |
| | 100% | 94.3 mg |

TABLE 20

Composition of Ex. 7 After Coating

| Ingredient | Percent | Amt/Unit |
|---|---|---|
| Hydromorphone beads | 84.8% | 84.2 mg |
| Aquacoat ® ECD 30 | 12.7% | 12.6 mg |
| Triethyl citrate | 0.9% | 2.5 mg |
| | 100% | 99.3 mg |

All three batches were cured in water loaded desiccators in a 60° C. oven. These batches were placed on screen trays in these desiccators after the Aquacoat® film was applied to the HPMC overcoated hydromorphone HCl bead. The desiccators containing the Aquacoat®-coated beads were then placed in a 60° C. oven for 72 hours. Thereafter, the batches were removed from the ovens. The beads appeared moist and therefore were dried in a lab line fluid bed dryer for one hour. They were then overcoated with 5% w/w Opadry® Y-5-1442 light pink in a Wurster insert.

Stability studies on Examples 5–7 show the initial dissolutions to be the same as dissolutions done on samples placed at 37° C./80% RH conditions. The results are provided in Tables 21–23 below:

TABLE 21

Dissolution (Time) — 5% Aquacoat ®

| Time (Days) | Wt (mg) | 1 hr | 2 hr | 4 hr | 8 hr | 12 hrs | 18 hrs | 24 hrs |
|---|---|---|---|---|---|---|---|---|
| Initial | 190 | 39.8 | 57.4 | 73.0 | 88.0 | 93.8 | 98.0 | 95.6 |
| 28 | 191 | 33.4 | 54.6 | 71.9 | 84.2 | 89.8 | 94.6 | 96.4 |

TABLE 22

Dissolution (Time) — 10% Aquacoat ®

| Time (Days) | Wt (mg) | 1 hr | 2 hr | 4 hr | 8 hr | 12 hrs | 18 hrs | 24 hrs |
|---|---|---|---|---|---|---|---|---|
| Initial | 200.3 | 7.5 | 27.9 | 48.5 | 68.1 | 76.2 | 90.3 | 88.9 |
| 28 | 210 | 9.9 | 32.4 | 52.6 | 67.8 | 77.9 | 85.9 | 90.9 |

TABLE 23

Dissolution (Time) — 15% Aquacoat ®

| Time (Days) | Wt (mg) | 1 hr | 2 hr | 4 hr | 8 hr | 12 hrs | 18 hrs | 24 hrs |
|---|---|---|---|---|---|---|---|---|
| Initial | 210 | 5.4 | 13.9 | 38.0 | 57.8 | 68.4 | 78.6 | 81.3 |
| 28 | 207.3 | 9.5 | 23.8 | 43.4 | 58.8 | 67.8 | 77.0 | 81.3 |

Example 8

In Example 8, Hydromorphone beads overcoated with 10% of the Aquacoat® are prepared in accordance with Example 6. The hydromorphone beads of Example 8 have the following formula set forth in Table 24 below:

TABLE 24

| Ingredient | Percent | Amt/Unit |
|---|---|---|
| Hydromorphone beads | 89.3% | 84.2 mg |
| Aquacoat ® ECD 30 | 8.9% | 8.4 mg |
| Triethyl citrate | 1.8% | 1.7 mg |
| | 100% | 94.3 mg |

To test the effectiveness of curing at a lower relative humidity compared to Example 6, the above beads were cured for 72 hours at 60° C. at 60% relative humidity (rather than 85% RH). Similar initial results were obtained for Example 8 as compared to Example 6, thus indicating that the curing step can also be completed at a lower relative humidity. The results are set forth in Table 25 below:

TABLE 25

Dissolution (Time) — 10% Aquacoat ®

| Example | 1 hr | 2 hr | 4 hr | 8 hr | 12 hr | 18 hr | 24 hr |
|---|---|---|---|---|---|---|---|
| Ex. 8 | 7.5 | 27.9 | 48.5 | 68.1 | 76.2 | 90.3 | 88.9 |
| Ex. 6 | 1.1 | 18.9 | 45.0 | 65.0 | 76.0 | 85.8 | 91.5 |

Examples 9–10

Hydromorphone HCl beads were prepared made by spraying a suspension of Hydromorphone HCl and Opadry® Y-5-1442 light pink (20% w/w) onto nu-pariel 18/20 beads, in accordance with the method set forth in Example 1. These beads were then further coated with Opadry® Y-5-1442 light pink (15% w/w). These beads were then further coated with the Surelease® at a level of 10% weight gain. The formula of the coated bead is set forth in Table 26:

TABLE 26

| Ingredient | mg/dose | Percent |
|---|---|---|
| Hydromorphone HCl | 4.0 mg | 4.32% |
| NuPariel beads 18/20 | 74.0 mg | 79.91% |
| Opadry light pink | 6.2 mg | 6.70% |
| Surelease | 8.4 mg | 9.07% |
| | 92.6 mg | 100% |

The batch was then divided into two portions. Example 9 was cured at 60° C./85% RH for 3 days (72 hours), and then dried in a fluid bed dryer for 30 minutes at 60° C. to dry off the excess moisture. These beads were then overcoated with 5% Opadry light pink. Example 10 was left uncured.

Both Examples 9 and 10 were then filled into hard gelatin capsules at a strength of 4 mg hydromorphone per capsule and stored for 3 months at 37° C./80% RH. Dissolution studies were conducted (pursuant to the method set forth for Example 1) initially for both Examples 9 and 10 and again after the 3 month storage at 37° C./85% RH. The results are set forth in Tables 27 and 28 below:

TABLE 27

Example 9

| Time | Initial | 3 Months at 37° C./80% RH |
|---|---|---|
| 1 | 4.7 | 6.5 |
| 4 | 42.3 | 56.0 |
| 8 | 64.9 | 75.0 |
| 12 | 77.2 | 83.19 |

TABLE 28

Example 10

| Time | Initial | 3 Months at 37° C./80% RH |
|---|---|---|
| 1 | 1.6 | 4.5 |
| 4 | 12.0 | 61.9 |
| 8 | 47.8 | 79.0 |
| 12 | 66.7 | 87.7 |

The results indicate that despite the expected differences in initial release rates caused by the use of a different aqueous dispersion of ethylcellulose (Surelease® as compared to Aquacoat®), the curing step as described above for Example 9 still significantly stabilized the product in comparison to the uncured product of Example 10. The relatively faster controlled release rate of the Examples using Aquacoat® as compared to Surelease® may be due to the lesser degree of plasticization during the preparation of the coating formulation. However, products using either coating may be modified to obtain satisfactory results.

Example 11

The following example illustrates the stabilization of morphine beads in accordance with the present invention.

A suspension of morphine sulphate and HPMC (Opadry® Clear Y-5-7095) was applied onto 18/20 mesh Nu-pariel beads in a fluid bed granulator with a Wurster column insert, at 60° C. A HPMC purple color suspension (Opadry® lavender YS-1-4729) was then applied as an overcoat at the same temperature. The beads were then overcoated to a 5% weight gain with Aquacoat® and triethyl citrate as a plasticizer at 60° C. inlet. The beads were then cured in an oven at 60° C./100% relative humidity for three days. The beads were then dried in the fluid bed granulator at 60° C., and an overcoat of HPMC with a purple color was then applied using the Wurster column.

The beads were then filled into hard gelatin capsules at a strength of 30 mg morphine sulphate per capsule. The final formula, set forth in Table 29 thus became:

TABLE 29

| Ingredient | mg/capsule | Percent |
|---|---|---|
| Morphine sulphate 5H$_2$O | 30.0 | 8.51% |
| Nu-pariel beads 18/20 | 255.0 | 72.36% |
| Opadry ® Clear Y-5-7095 | 15.0 | 4.26% |
| Opadry ® Lavender YS-1-4729 | 15.8 | 4.48% |
| Aquacoat ® ECD30 (solids) | 15.8 | 4.48% |

TABLE 29-continued

| Ingredient | mg/capsule | Percent |
|---|---|---|
| Triethyl citrate | 3.2 | 0.91% |
| Opadry Lavender Y-S-1-4729 | 17.6 | 4.99% |
| | 352.4 | 100% |

An initial dissolution of the capsules was conducted using the USP paddle method at 100 rpm in 900 ml of water, and again after storage at 37° C./80% relative humidity, and at 60° C. dry for one month. It was observed that a stable product was made. The results are set forth in Table 30:

TABLE 30

Percent Morphine Dissolved

| Time Hrs | Initial | 37° C./80% RH after 1 Mo | 60° C. after 1 Mo |
|---|---|---|---|
| 1 | 15.7 | 16.6 | 15.3 |
| 4 | 53.0 | 51.4 | 54.9 |
| 8 | 84.4 | 83.3 | 90.4 |
| 12 | 96.5 | 94.4 | 96.9 |

Example 12

A second experiment was conducted with morphine as described in Example 11; however, the retardant Aquacoat® layer was applied to a 15% weight gain to develop a slower releasing morphine product. The final formulation is set forth in Table 31:

TABLE 31

| Ingredient | Mg/capsule | Percent |
|---|---|---|
| Morphine sulphate 5H$_2$O | 30.0 | 7.65% |
| Nu-pariel beads 18/20 | 255.0 | 65.0% |
| Opadry ® Clear Y-5-7095 | 15.0 | 3.82% |
| Opadry ® Lavender YS-1-4729 | 15.8 | 4.03% |
| Aquacoat ® ECD30 (solids) | 47.4 | 12.08% |
| Triethyl citrate | 9.5 | 2.42% |
| Opadry Lavender Y-S-1-4729 | 19.6 | 5.00% |
| | 392.3 | 100% |

An initial dissolution of the 30 mg morphine sulphate capsules was conducted as described in Example 10 and again after storage at 37° C./100% relative humidity and 60° C. dry for one month. It was again observed that a stable product was made. The results are set forth in Table 32 below:

TABLE 32

Percent Morphine Dissolved

| Time Hrs | Initial | 37° C./80% RH After 1 Mo | 60° C. After 1 Mo |
|---|---|---|---|
| 1 | 0 | 3.1 | 0 |
| 4 | 18.1 | 19.4 | 17.8 |
| 8 | 49.2 | 49.4 | 45.7 |
| 12 | 66.3 | 68.2 | 65.9 |

Examples 13–14

In Example 13, the applicability of another medicament, theophylline, having very different physical properties compared to hydromorphone is demonstrated.

Theophylline hydrous and colloidal silicon dioxide were first mixed together in a high shear mixer, then sieved using a Jet sieve to enhance flowability. Using a fluid bed granulator equipped with a rotor processor, sugar spheres were layered with the theophylline/colloidal silicon dioxide mixture using a PVP (C-30) solution. Layering was continued until an approximately 78% load was obtained.

The formula of the 400 mg theophylline beads when filled into capsules is set forth in Table 33 as follows:

TABLE 33

|  | Mg/unit capsules |
|---|---|
| Theophylline hydrous (equivalent to 400 mg anhydrous theophylline) | 440.0 |
| Colloidal silicon dioxide | 0.4 |
| Sugar spheres 30/35 mesh | 110.0 |
| PVP (C-30) | 13.5 |
|  | 563.9 |

These spheres were then overcoated with a dibutylsebecate plasticized Aquacoat® ECD 30 retardant to a 5% weight gain in the Wurster column in a fluid bed granulator. A portion of the spheres was not cured, and another portion was stored at 60° C. and 100% relative humidity for 72 hours. The following results set forth in Table 34 were obtained:

TABLE 34

|  | 1 hr | 2 hr | 3 hr | 4 hr | 6 hr | 8 hr | 24 hr |
|---|---|---|---|---|---|---|---|
| Initial (uncured) | 9.0 | 92.8 | 94.6 | 95.4 | 97.8 | 98.0 | 100.0 |
| 72 hours at 60° C./85% RH | 3.2 | 5.3 | 7.0 | 7.9 | 11.0 | 14.1 | 35.8 |

From the above, it was determined that theophylline spheroids coated with Aquacoat® also are not stable and need to be cured. After storage at 72 hours at 60° C. and 85% relative humidity, a dramatic drop in dissolution rate occurred; however, such condition may, in some instances, represent "ideal" curing conditions to form a stable product. In view of this goal, the dissolution date after 72 hours at 60° C./85% RH provides too slow a dissolution profile for theophylline.

Therefore, Example 14 was prepared in order to attempt to improve the dissolution profile of the formulation via incorporation of this new curing step, and the coating was altered in order to increase the dissolution rate to 100% theophylline dissolved in 12 hours.

Example 14 was prepared as follows. Theophylline powder layered beads were made as described in Example 13 and were then overcoated with a plasticized Aquacoat® ECD 30 retardant, which, and for this example, included 10% HPMC (hydroxypropyl methyl cellulose). This was done so that the release of theophylline would be faster than Example 13. The inclusion of HPMC to speed up dissolution is known in the prior art. The retardant layer was also coated to a 6% weight gain in the Wurster column of the fluid bed granulator.

The coated beads were then cured for 72 hours at 60° C./85% relative humidity. A dissolution study was conducted initially, and once again after the beads were stored at 37° C./80% relative humidity for three months. It was observed that the stability of the dissolution of the theophylline from the formulation of Example 14 improved dramatically compared to Example 13. It was further observed that by inclusion of HPMC in the retardant layer in the proportions of Aquacoat® ECD 30 (solids):HPMC of 9:1, coated to a 6% weight gain, the dissolution rate of the formulation was increased to 100% theophylline dissolved in 12 hours. The results are set forth in detail in Table 35 below:

TABLE 35

|  | 1 hr | 2 hr | 4 hr | 8 hr | 12 hr |
|---|---|---|---|---|---|
| Cured Initial | 17 | 38 | 68 | 97 | 100 |
| Storage at 37° C./80% RH for 3 months | 13 | 31 | 60 | 94 | 100 |

The examples provided above are not meant to be exclusive. Many other variations of the present invention would be obvious to those skilled in the art.

For example, although the present invention has been described with respect to the most preferred hydrophobic polymer, ethycellulose, it is contemplated that other hydrophobic polymers, such as other cellulose derivatives, may also be useful in conjunction with the present invention. Such other hydrophobic polymers are considered to be within the scope of the appended claims.

Likewise, as previously explained, one skilled in the art will recognize that necessary curing conditions may be change somewhat depending upon the particular formulation (including the amount of overcoating, the properties of the therapeutically active agent, etc.), such that a stabilized product is obtained via a modified range with regard to temperature, humidity and time. Such variations are contemplated to be within the scope of the appended claims.

What is claimed is:

1. A controlled release layered bead for inclusion in an oral controlled release pharmaceutical formulation comprising
    an inert bead coated with an analgesic,
    a barrier layer over said bead coated with said analgesic, said barrier layer comprising hydroxypropylmethylcellulose,
    a controlled release layer over said barrier layer derived from an aqueous dispersion of plasticized ethylcellulose in an amount sufficient to obtain a controlled release of said analgesic when said formulation is exposed to an environmental fluid, said controlled release layered bead being cured to a temperature greater than the glass transition temperature of the plasticized ethylcellulose for at least about 24 hours.

2. The controlled release layered bead of claim 1, wherein said barrier layered bead is coated to a weight gain from about 2 to about 30% with said controlled release layer.

3. The controlled release layered bead of claim 1, further comprising a second barrier layer over said controlled release layer, said second barrier layer comprising hydroxypropylmethylcellulose.

4. The controlled release layered bead of claim 1, wherein said controlled release layer further comprises a release-modifying agent in an amount effective to modify the rate of release of said analgesic from said cured, coated bead.

5. The controlled release layered bead of claim 4, wherein said release-modifying agent is selected from the group consisting of a hydrophilic polymer, a semi-permeable polymer, an erosion-promoting polymer, an agent capable of making microporous lamina, a poreformer and mixtures of any of the foregoing.

6. The controlled release layered bead of claim 5, wherein said controlled release layer comprises from about 0.1% to about 70% of said release-modifying agent.

7. The controlled release layered bead of claim 6, wherein said release-modifying agent is selected from the group consisting of hydroxypropylmethylcellulose, lactose, metal stearates and mixtures of any of the foregoing.

8. The controlled release layered bead of claim 1, wherein a portion of the amount of said analgesic included in said bead is incorporated into an outer coating.

9. A method for preparing a controlled release layered bead for inclusion in an oral controlled release formulation of an analgesic, comprising:

coating a pharmaceutically acceptable inert bead with an analgesic;

thereafter coating said bead with a barrier layer comprising hydroxypropylmethylcellulose;

thereafter applying a controlled release layer onto said bead, said controlled release layer comprising a sufficient amount of a plasticized ethylcellulose to obtain a predetermined controlled release of said analgesic when said coated bead is exposed to an environmental fluid, said plasticized ethylcellulose being applied to said bead as an aqueous dispersion; and curing said controlled release layered bead at a temperature greater than the glass transition temperature of the plasticized ethylcellulose for at least 24 hours.

10. The method of claim 9, further comprising coating said controlled release bead with an outer layer comprising said analgesic.

11. The method of claim 9, further comprising applying said controlled release layer onto said bead to a weight gain from about 2 to about 25%.

12. The method of claim 9, further comprising adding a release-modifying agent to said controlled release layer in an amount effective to modify the rate of release of said analgesic from said cured, coated bead.

13. The method of claim 12, wherein said release-modifying agent is selected from the group consisting of a hydrophilic polymer, a semi-permeable polymer, an erosion-promoting polymer, an agent capable of making microporous lamina, a pore-former, and mixtures of any of the foregoing.

14. The method of claim 13, wherein said controlled release layer comprises from about 0.1% to about 70% of said release-modifying agent.

15. The method of claim 14, wherein said controlled release layer comprises from about 0.1% to about 50% of said release-modifying agent.

16. The method of claim 15, wherein said controlled release layer comprises from about 0.1% to about 25% of said release-modifying agent.

17. The method of claim 12, wherein said release-modifying agent is selected from the group consisting of hydroxypropylmethylcellulose, lactose, metal stearates, and mixtures of any of the foregoing.

18. The method of claim 9, further comprising overcoating said controlled release bead with a second barrier layer comprising hydroxypropylmethylcellulose.

19. The method of claim 9, further comprising the step of overcoating said controlled release bead with an outer layer comprising said analgesic.

20. The method of claim 19, wherein said outer layer comprises hydroxypropylmethylcellulose.

21. A controlled release layered bead for inclusion in a controlled release pharmaceutical formulation, comprising a pharmaceutically acceptable inert bead coated with an analgesic, said bead coated with said analgestic being overcoated with a barrier layer comprising hydroxypropylmethylcellulose, said barrier coated bead being coated with a controlled release layer derived from an aqueous dispersion of plasticized ethylcellulose in an amount sufficient to obtain a controlled release of said analgesic when said bead is exposed to a gastrointestinal fluid, said coated bead being cured at a temperature greater than the glass transition temperature of the plasticized ethylcellulose for at least about 24 hours, to cause individual ethylcellulose particles in said coating to coalesce and to gradually slow the release of said analgesic when said bead is exposed to aqueous fluid, until an endpoint is reached at which said cured coated bead, when subjected to in-vitro dissolution, releases said analgesic in amounts which do not vary at any time point along the dissolution curve by more than about 20% of the total amount of analgesic released, when compared to the in-vitro dissolution of said coated bead prior to curing.

22. The controlled release layered bead of claim 21, wherein said cured, coated bead provides the same rate of release immediately after curing to said endpoint, and after subsequent exposure to accelerated storage conditions of one month at a temperature of 37° C. and at a relative humidity of 80%.

23. The controlled release layered bead of claim 21, wherein said cured, coated bead provides the same rate of release immediately after curing to said endpoint, and after subsequent exposure to accelerated storage conditions of one month at a temperature of 40° C. and at a relative humidity of 75%.

24. The controlled release layered bead of claim 21, wherein said controlled release layer is applied on said barrier coated bead to a weight gain from about 2% to about 25%.

25. The controlled release layered bead of claim 21, which includes said controlled released layer sufficient to obtain a controlled release of said analgesic when measured by the USP Paddle Method of U.S. Pharmacopeia XXII (1990) at 100 rpm at 900 ml aqueous buffer (pH between 1.6 and 7.2) at 37° C. from about 12.5% to about 42.5% (by wt) analgesic released after 1 hour, from about 25% to about 55% (by wt) analgesic released after 2 hours, from about 45% to about 75% (by wt) analgesic released after 4 hours and from about 55% to about 85% (by wt) analgesic released after 8 hours.

26. The controlled release layered bead of claim 21, wherein said controlled release layer further comprises a release-modifying agent in an amount effective to modify the rate of release of said analgesic from said cured, coated bead.

27. The controlled release layered bead of claim 26, wherein said release-modifying agent is selected from the group consisting of a hydrophilic polymer, a semi-permeable polymer, an erosion-promoting polymer, an agent capable of making microporous lamina, a poreformer and mixtures of any of the foregoing.

28. The controlled release layered bead of claim 21, wherein said analgesic is morphine or a pharmceutically acceptable salt therof.

29. The controlled release layered bead of claim 21, further comprising a second barrier layer overcoated on said controlled release layer.

30. The controlled release layered bead of claim 29, wherein said second barrier layer comprises hydroxypropylmethylcellulose.

31. The controlled release layered bead of claim 30, further comprising an outer coating comprising a loading dose of said analgesic.

* * * * *